United States Patent [19]

Ito et al.

[11] 4,450,267
[45] May 22, 1984

[54] LATENT CURING AGENTS FOR EPOXY RESINS

[75] Inventors: Nobuo Ito, Ooisomachi; Koji Takeuchi, Yokohama; Masahiro Abe, Kawasaki; Tsuneo Ishiguro, Yokosuka, all of Japan

[73] Assignee: Ajinomoto Company Incorporated, Tokyo, Japan

[21] Appl. No.: 459,214

[22] Filed: Jan. 19, 1983

[30] Foreign Application Priority Data

Jan. 29, 1982 [JP] Japan .................................. 57-12891

[51] Int. Cl.³ ............................................ C08G 59/44
[52] U.S. Cl. ...................................... 528/99; 525/504; 564/150
[58] Field of Search .......................... 528/99; 564/150; 525/504

[56] References Cited

U.S. PATENT DOCUMENTS 2,847,395  8/1958  Wear ................................. 528/123 X
3,467,707  9/1969  Aelony ............................. 528/123 X
3,530,173  9/1970  Aelony ............................. 528/99 X Primary Examiner—Earl A. Nielsen
Attorney, Agent, or Firm—Oblon, Fisher, Spivak, McClelland & Maier

[57] ABSTRACT

Hydrazides of the formula

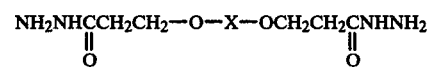

are good curing agents for epoxy resin, wherein in the formula, X is an aromatic hydrocarbon residue of dihydric phenol,

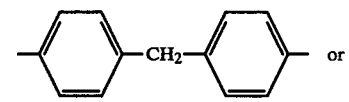 or

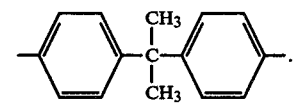

The curing agents are useful in formulating novel storable one-package, heat-curable epoxy resin-based compositions.

13 Claims, No Drawings

LATENT CURING AGENTS FOR EPOXY RESINS

BACKGROUND OF THE INVENTION

1. Field of the Invention

The present invention relates to certain novel hydrazides and the use thereof as curing agents for epoxy resins.

2. Description of the Prior Art

Epoxy resins are widely employed as electric insulating materials, various moulded products, adhesives or coatings because they give valuable cured resins having excellent mechanical, electrical and chemical properties when cured with suitable curing agents, for example acid anhydride and amine curing agents. However, epoxy resin composition incorporating amine curing agents are cured rapidly at ordinary temperature and at elevated temperature, and hence they lack storage stability. Also, epoxy resin compositions incorporating acid anhydride curing agents are stable at ordinary temperature, but heating for a long period of time at elevated temperature is required for full curing. Usually, tertiary amines, quaternary ammonium compounds or organo metal complexes are further added to the composition for the purpose of accelerating curing rate. However, the addition of such cure accelerator impairs storage stability markedly.

So-called latent curing agents which are compatible with epoxy resins to form a composition which is stable at relatively low temperature and which is rapidly cured when heated to elevated temperature are eagerly desired. In the field of coating, particularly, curing agents are desired which give colorless and transparent cured epoxy resin, from the view of tone of color. Representative compounds which have been heretofore proposed as latent curing agents are dicyandiamide, dibasic acid hydrazide, boron trifluoride-amine adduct, guanamine and melamine. Among these compounds, dicyandiamide, dibasic acid hydrazide and quanamine are useful in formulating epoxy resin compositions having excellent storage stability, but full curing by means of these compounds could be achieved only by heating at higher temperature than 150° C. for a long time. Also, boron trifluoride-amine adduct is hard to treat owing to its high hygroscopic property, and it affects the physical properties of the cured resin adversely.

There has been heretofore known almost no latent epoxy curing agent which causes rapid curing at moderate elevated temperature (that is 100° C.-150° C.) and which gives an epoxy resin composition having excellent storage stability at ordinary temperature.

SUMMARY OF THE INVENTION

An object of the present invention is to provide novel hydrazide-type curing agents which are useful in making storable one-package curable epoxy resin compositions.

Another object of the present invention is to provide hydrazide-type curing agents which alone or together with other curing agents can activate a rapid curing of epoxy resin composition at relatively low temperatures and yet be extraordinarily resistant to gelling at 40° C. for three or more weeks.

A further object of the present invention is to provide hydrazide-type curing agents which give cured epoxy resin having excellent transparency and water resistance.

The above objects of the present invention may be substantially achieved by providing as a curing agent a hydrazide compound having the following general formula (I):

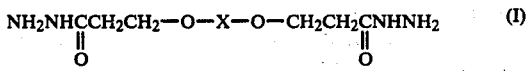

wherein X is an aromatic hydrocarbon residue of a dihydric phenol,

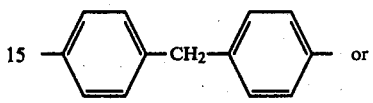 or

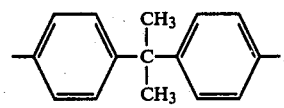

DESCRIPTION OF THE PREFERRED EMBODIMENTS

The hydrazides which may be represented by the above general formula (I) may be readily prepared by reacting an adduct of 1 mole of aromatic diol represented by the general formula OH—X—OH wherein X has the meanings set forth above and 2 moles of alkyl acrylate having the general formula $CH_2=CHCOOR$ wherein R is alkyl group, with hydrazine hydrate, said adduct of aromatic diol and bimolecular alkyl acrylate being represented by the following general formula (a)

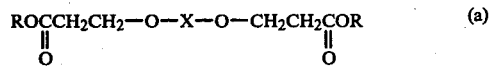

wherein X has the meanings set forth above and R is alkyl group having 1-4 carbon atoms.

Although the aromatic diol-bimolecular alkyl acrylate adduct may be directly prepared by the addition reaction between an aromatic diol and alkyl acrylate, it may also be prepared by the following two-step reaction. That is, 1 mole of aromatic diol is reacted with 2 moles of acrylonitrile to form an aromatic diol-bimolecular acrylonitrile adduct, which is then subjected to alcoholysis whereby the nitrile group in the adduct is converted into a carboalkoxy group, said aromatic diol-bimolecular acrylonitrile adduct being represented by the general formula (b)

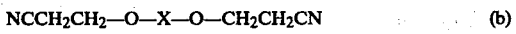

wherein X has the meanings set forth above.

Preferred specific examples of the aromatic diols are catechol, resorcinol, hydroquinone, bisphenol A and bisphenol F.

The preparation of the aromatic diol-bimolecular alkyl acrylate may be carried out by heating an aromatic diol and an alkyl acrylate in the presence of a basic catalyst such as potassium hydroxide in the absence or presence of solvents such as methanol and ethanol at reflux temperature for several hours, the amount of alkyl acrylate being at least 2 times the amount of the aromatic diol (mole basis).

The preparation of the aromatic diol-bimolecular alkyl acrylate adduct starting from an aromatic diol and acrylonitrile may be accomplished by the process wherein 1 mole of aromatic diol is reacted with at least 2 moles of acrylonitrile in the presence of a basic catalyst with or without solvent similarly with the reaction between aromatic diol and alkyl acrylate at reflux temperature for 15–20 hours or at 130°–140° C. for several hours in an autoclave to obtain an aromatic diol-bimolecular acrylonitrile adduct (b), which is then heated in a mixed solution of 5% aqueous alcohol and acid at reflux temperature for several hours, the respective amount of alcohol and acid being at least 2 times the amount of the adduct (mole basis).

The alkyl acrylate to be reacted with the aromatic diol is not particularly limited. Usually a lower alkyl ester of 1–4 carbon atoms is employed. Especially a, methyl ester is practical.

The alcohol which is employed for preparation of the aromatic diol-bimolecular alkyl acrylate adduct from the aromatic diol-bimolecular acrylonitrile adduct is not particularly limited, but methanol and ethanol are practical.

Suitable examples of basic catalysts which can be used in the reaction system are potassium hydroxide, sodium methoxide and benzyltrimethylammonium hydroxide. The amount of basic catalyst may be about 1–2 percent by weight based on the aromatic diol. The addition reaction is carried out in the presence of a polymerization inhibitor such as hydroquinone. After the addition reaction has been completed, excess acrylic ester and solvent if any are removed from the reaction mixture by distillation.

The aromatic diol-bimolecular acrylic ester adduct (a) obtained thusly is further reacted with hydrazine hydrate in the presence of a solvent such as methanol or ethanol at room temperature for several hours, the amount employed of hydrazine hydrate being at least 2 times (mole basis) the amount of the adduct (a). The reaction may be carried out at reflux temperature if necessary.

After the completion of the reaction, excess hydrated hydrazine and the solvent are removed from the reaction mixture by distillation, and the precipitated hydrazide is separated and recrystallized from a suitable solvent such as methanol, ethanol or water. The hydrazide of the present invention may be pulverized in fine particles.

The hitherto known dibasic acid hydrazides, such as adipic acid hydrazide, sebacic acid hydrazide, isophthalic acid hydrazide and the like, are high melting compound above 180° C., and the epoxy resin compositions incorporating such dibasic acid hydrazides is cured when heated to 150° C. or higher temperatures. Contrary thereto, the hydrazides of the present invention are relatively low melting compounds and provide, when incorporated into an epoxy resin, curable composition which are stable for periods of several weeks at 40° C. and which can thereafter be readily cured at temperatures of as low as about 120°–140° C. to give a colorless, transparent and tough cured product having excellent water resistance.

The required amount of curing agent is determined by the number of active hydrogen atoms in the curing agent employed and the number of epoxy groups in the epoxy resins. In general, 0.5–1.5, preferably 0.7–1.2, active hydrogen equivalent weight per epoxy equivalent weight is employed.

As epoxy resins which may be applied to the hydrazide curing agents of the present invention, various well-known ones having an average of more than 1 epoxy groups in the molecule may be employed. Representative epoxy resins are those based on glycidyl ethers of polyhydric phenols such as 2,2-bis(4-hydroxyphenyl)-propane (Bisphenol A), resorcinol, hydroquinone, pyrocatechol, saligenin, glycidyl ether of Bisphenol F and glycidyl ether of phenolformaldehyde resin.

If necessary, other curing agents, cure accelerators and fillers may be employed in combination with the curing agent of the present invention.

The following examples illustrate the preparation of the hydrazides of the present invention.

EXAMPLE 1

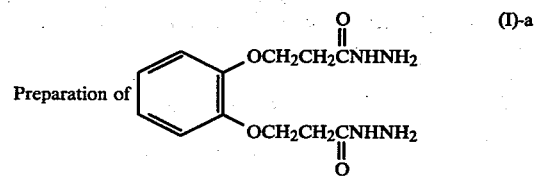

Preparation of (I)-a 25 g (0.227 mole) of catechol, 75 g (1.42 mole) of acrylonitrile, and 0.5 g of sodium methylate were mixed in a 300 ml three-necked flask equipped with a reflux condensor and a stirrer. The mixture was heated under reflux for 20 hours and the reaction mixture was dissolved in benzene. After washing three times with 100 ml of water, benzene and excess acrylonitrile were removed under reduced pressure to obtain the viscous liquid. To this compound, 50 ml of methanol was added, and the mixture was stirred to precipitate the crystals. After filtration, the crystals were washed with methanol and dried in vacuo to obtain 11.2 g of the bimolecular acrylonitrile adduct of catechol (I)-a″. mp 120°~122° C.

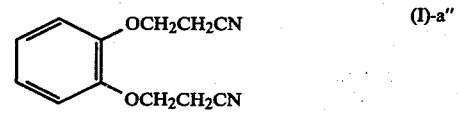

(I)-a″

A mixture of 1% methanol solution and sulfuric acid (each 30 g) was added to 8 g (0.037 mole) of the adduct thus obtained and was heated under reflux for 7 hours with stirring. To this reaction mixture, 100 ml of water was added to dissolve the produced ammonium sulfate crystals. Then 300 ml of ethyl ether was added to extract the reactor. After washing the extract with 100 ml of 5% sodium hydroxide solution and three times with 100 ml of water, ethyl ether was removed under reduced pressure to obtain 4.6 g of the adduct of catechol and bimolecular methyl acrylate (I-a′).

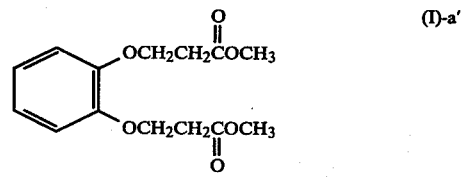

(I)-a′

4.5 g (0.028 mole) of the adduct thus obtained and 10 g (0.16 mole) of 80% hydrazine hydrate solution were mixed in a 100 ml three-necked flask equipped with a stirrer. To this mixture, 50 ml of methanol was added and then was allowed to react at 50° C. for 2 hours with stirring. After cooling, the precipitated crystals were filtered, washed with methanol, and dried in vacuo to obtain the target product as white needles.

The analytical values are shown below.

| Melting point | 145~146° C. | | |
|---|---|---|---|
| Elemental analysis | C | H | N (%) |
| Found | 51.27 | 6.42 | 19.71 |
| Calculated for $C_{12}H_{18}O_4N_4$ | 51.06 | 6.38 | 19.86 |
| Field desorption mass spectrum | $[M + H]^+$ at m/e 283 | | |

EXAMPLE 2

Preparation of

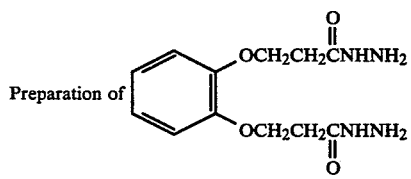
(I)-b 35 g (0.318 mole) of resorcinol, 350 ml (3.89 mole) of methyl acrylate, and 0.7 g of potassium hydroxide were mixed in the same flask described in Example 1, and the mixture was heated under reflux for 7 hours with stirring. To the reaction mixture, 4.6 ml of 10% hydrochloric acid solution was added, and excess methyl acrylate was removed under reduced pressure. Then, 1000 ml of ethyl ether was added, and insoluble material (potassium chloride) was filtered out. The residue was washed with 100 ml of 10% sodium hydroxide solution and three times with 100 ml of water, and ethyl ether was removed in vacuo to obtain 33.4 g of the adduct of resorcinol and bimolecular methyl acrylate (I-b', mp 74°~76° C., white needles).

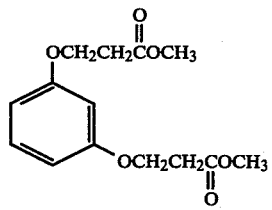
(I)-b'

32.3 g (0.115 mole) of the adduct of resorcinol and bimolecular methyl acrylate thus obtained was dissolved in 600 ml of methanol. To this solution, 115 ml (1.84 mole) of 80% hydrazine hydrate solution was added and was allowed to react at 50° C. for 2 hours with stirring. From the reaction mixture, excess hydrazine hydrate and methanol was removed under reduced pressure. The residue was washed with methanol and dried in vacuo to obtain 26.1 g of the target product as white powder.

The analytical values are shown below.

| Melting point | 143~144° C. | | |
|---|---|---|---|
| Elemental analysis | C | H | N (%) |
| Found | 50.91 | 6.40 | 19.82 |
| Calculated for $C_{12}H_{18}O_4N_4$ | 51.06 | 6.38 | 19.86 |
| Nuclear magnetic resonance spectrum | | | |
| δ(DMSO—$d_6$/TMS) | | | |

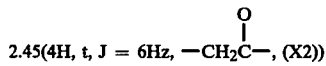

2.45(4H, t, J = 6Hz, —CH$_2$C—, (X2))

3.1~3.6(4H, br, —NH$_2$, (X2))
4.08(4H, t, J = 6Hz, —OCH$_2$CH$_2$, (X2))
6.3~6.5(3H, m, arom)
8.9~9.1(2H, br, —NHNH$_2$, (X2))
Field desorption mass spectrum $[M + H]^+$ at m/e 283

EXAMPLE 3

Preparation of 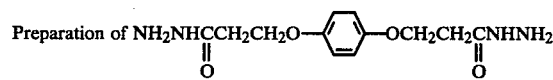 (I)-c

According to the procedure described in Example 1, 25 g (0.227 mole) of hydroquinone, 75 g (1.42 mole) of acrylonitrile and 0.6 g of sodium methoxide were mixed and were allowed to react to obtain 35.5 g of the bimolecular acrylonitrile adduct of hydroquinone (I-c″).

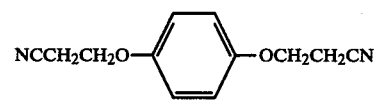
(I)-c″

To 25 g (0.153 mole) of the adduct thus obtained, a mixture of 5% methanol solution and sulfuric acid (each 70 g) was added. Thereafter, the procedure of Example 1 was repeated to obtain 28.0 g of the adduct of hydroquinone and bimolecular methyl acrylate (I-c').

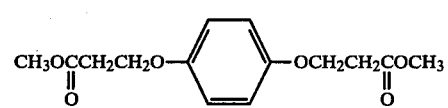
(I)-c'

18.0 g (0.063 mole) of the adduct of hydroquinone and methyl acrylate thus obtained were dissolved in 180 ml of methanol, and then 32 g (0.512 mole) of 80% hydrazine hydrate solution were added. The mixture was allowed to react according to the procedure described in Example 1. 16.5 g of the target product were obtained.

The analytical values are shown below.

| Melting point | 173~175° C. | | |
|---|---|---|---|
| Elemental analysis | C | H | N (%) |
| Found | 51.33 | 6.48 | 19.63 |
| Calculated for $C_{12}H_{18}N_4O_4$ | 51.06 | 6.38 | 19.86 |
| Field desorption mass spectrum | $[M + H]^+$ at m/e 283 | | |

EXAMPLE 4

Preparation of 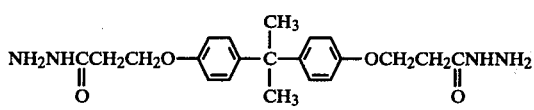 (I)-d 40 g (0.175 mole) of bisphenol A, 315 ml (3.5 mole) of methyl acrylate, and 6.5 ml of 10% benzyltrimethylammonium hydroxide solution were mixed in the same flask described in Example 1, and the mixture was heated under reflux for 48 hours with stirring. After cooling to room temperature, 7.3 ml of 10% hydrochloric acid solution was added, and then excess methyl acrylate was removed in vacuo. The residue was dissolved in 1000 ml of ethyl acetate and washed successively with 200 ml of 10% hydrochloric acid solution, pure water, 10% sodium hydroxide solution, and twice with saturated sodium chloride solution. Then ethyl acetate was removed to obtain 27.7 g of the colorless oily substance. The oily substance thus obtained was purified by silica gel column chromatography using a mixture of toluene-acetic acid as an eluent to obtain 10.6 g of the bimolecular methyl acrylate adduct of bisphenol A (I-d').

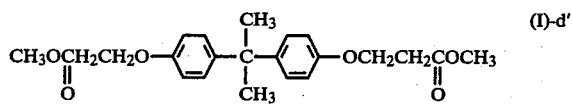

10.0 g (0.025 mole) of the adduct thus obtained, 100 ml of methanol, and 16 ml (0.25 mole) of 80% hydrazine hydrate solution were mixed and allowed to react at room temperature for 5 hours with stirring. From the reaction mixture, excess hydrazine hydrate and methanol were removed under the reduced pressure, and then 50 ml of ethanol was added to the residue to precipitate the crystals. After filtration, the crystals were recrystallized from ethanol and dried in vacuo to obtain 8.26 g of the target product as a white powder.
The analytical values are shown below.

| Melting point | 136~140° C. | | |
|---|---|---|---|
| Elemental analysis | C | H | N (%) |
| Found | 62.75 | 6.91 | 14.11 |
| Calculated for $C_{21}H_{28}N_4O_4$ | 62.98 | 7.05 | 13.99 |
| Nuclear magnetic resonance spectrum | | | |
| $\delta$(DMSO-$d_6$/TMS) | | | |
| 1.58(6H, s, $CH_3$—C—$CH_3$) | | | |
| 2.52(4H, t, J = 6Hz, —$CH_2$C—, (X2)) | | | |
| 4.17(4H, t, J = 6Hz, —$OCH_2CH_2$—, (X2)) | | | |
| 3.0 4.5(4H, br, —$NHNH_2$, (X2)) | | | |
| 6.82(4H, d, J = 9Hz, arom) | | | |
| 7.13(4H, d, J = 9Hz, arom) | | | |
| 8.9 9.2(2H, br, —$NHNH_2$, (X2)) | | | |
| Field desorption mass spectrum | $[M + H]^+$ at m/e 401 | | |

EXAMPLE 5

Preparation of (I)-e

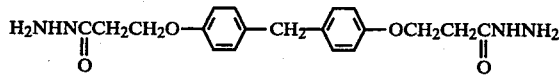

In an autoclave equipped with an electromagnetic stirrer, 40 g (0.2 mole) of bisphenol F, 27.6 g (0.52 mole) of acrylonitrile, and 0.5 g of sodium methylate were mixed. After nitrogen was substituted for air, the mixture was heated at 130°~140° C. for 5 hours with stirring. After cooling, the reaction mixture was dissolved in 300 ml of benzene and washed successively with 200 ml of 5% sodium hydroxide solution and 300 ml of water. Then the benzene layer was concentrated, and 100 ml of methanol was added to precipitate the crystals. After filtration, the crystals were dried in vacuo to obtain 6.04 g of the adduct of bisphenol F and bimolecular acrylonitrile (I-e"). mp 100°~102° C.

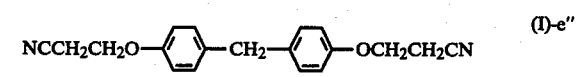

The mixture of 5% methanol solution (30 g) and sulfuric acid (30 g) was added to 6.0 g (0.0237 mole) of the adduct thus obtained and heated under reflux for 5 hours with stirring, and then 300 ml of toluene was added. After being washed successively with 200 ml of water, 100 ml of 5% sodium hydroxide solution and 300 ml of water, the solution was concentrated and dried to obtain 5.65 g of white solid substance (I-e').

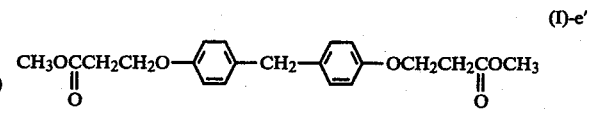

5.65 g (0.015 mole) of the compound thus obtained was dissolved in 56 ml of methanol, and then 8.8 g (0.141 mole) of 80% hydrazine hydrate solution was added. The mixture was allowed to react at 50° C. for 2 hours with stirring. After filtration, the crystals were washed with methanol and dried in vacuo to obtain 4.16 g of the target product as white powder.
The analytical values are shown below.

| Melting point | 182~183° C. | | |
|---|---|---|---|
| Elemental analysis | C | H | N (%) |
| Found | 61.48 | 6.53 | 14.87 |
| Calculated for $C_{19}H_{24}N_4O_4$ | 61.29 | 6.45 | 15.05 |
| Field desorption mass spectrum | $[M + H]^+$ at m/e 373 | | |

EXAMPLE 6

Reactivity, water resistance, and storage stability of the formulated epoxy resin were evaluated.
1. Preparation of the sample
The formulation of each sample is shown in Table 1. Each sample was stirred for 1 hour with defoaming under reduced pressure by using a mixing and grinding machine.
2. Evaluation of the reactivity
(1) The sample was put into a gear oven for 60 minutes and cured temperature was measured.
(2) The sample was heated at 150° C. for 60 minutes and then at 60° C. for 180 minutes. The resulting cured resin was observed with the naked eye.
3. Water resistance
1 g of the sample was put into a frame of 25 mm diameter and heated at 150° C. for 60 minutes and then at 160° C. for 180 minutes. The cured resin thus obtained was soaked in 50 cc of 40° C. hot water, and the weight change was measured.
4. Storage stability
The sample was put into a gear oven set to 40° C., and the day required for the sample becoming non-fluidity was measured.

TABLE 1

| | Formulation No. | | | | | | | |
|---|---|---|---|---|---|---|---|---|
| | 1 | 2 | 3 | 4 | 5 | 6 | 7 | 8 |
| Epon 828*1 | 100 | 100 | 100 | 100 | 100 | 100 | 100 | 100 |
| Sample (I)-a | 37 | | | | | | | |

TABLE 1-continued

| | Formulation No. | | | | | | | |
|---|---|---|---|---|---|---|---|---|
| | 1 | 2 | 3 | 4 | 5 | 6 | 7 | 8 |
| Sample (I)-b | 37 | | | | | | | |
| Sample (I)-c | | 37 | | | | | | |
| Sample (I)-d | | | 52 | | | | | |
| Sample (I)-e | | | | 49 | | | | |
| Adipic dihydride | | | | | 23 | | | |
| Isophtalic dihydride | | | | | | 26 | | |
| Dicyandiamide | | | | | | | | 28 |

*[1] A product of Shell Chemical Co. bisphenol A type epoxy resin having epoxy equivalent of 175~210.

TABLE 2

Cured temperature

| Formulation No. | Cured Temperature |
|---|---|
| No. 1 | 120° C. |
| No. 2 | 120 |
| No. 3 | 140 |
| No. 4 | 120 |
| No. 5 | 140 |
| No. 6 | 160 |
| No. 7 | 160 |
| No. 8 | 180 |

TABLE 3

Appearance of the cured resin

| Formulation No. | Appearance |
|---|---|
| No. 1 | Stiff and transparent material |
| No. 2 | Stiff and transparent material |
| No. 3 | Stiff and transparent material |
| No. 4 | Stiff and transparent material |
| No. 5 | Stiff and transparent material |
| No. 6 | Opaque white colored material |
| No. 7 | Opaque white colored gel |
| No. 8 | Less transparent material |

TABLE 4

Water resistance

| Formulation No. | Water absorption |
|---|---|
| No. 1 | + 1.8 wt % |
| No. 2 | 1.7 |
| No. 3 | 1.5 |
| No. 4 | 1.6 |
| No. 5 | 1.8 |
| No. 6 | 2.9 |
| No. 7 | 1.8 |
| No. 8 | —*[1] |

*[1] cannot be measured because the sample was not full-cured

TABLE 5

Storage stability

| Formulation No. | Storage stability |
|---|---|
| No. 1 | >4 weeks |
| No. 2 | " |
| No. 3 | " |
| No. 4 | " |
| No. 5 | " |
| No. 6 | " |
| No. 7 | " |
| No. 8 | " |

The results of Table 2~5 shows that the curing agent for epoxy resin in this invention has excellent storage stability, reactivity, and water resistance.

Especially, the reactivity of this agent is superior and the resulting cured resin is stiff and transparent compared with that of the control agent.

What we claim is:

1. A compound having the formula

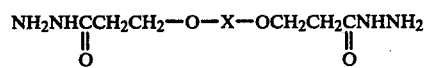

wherein X is an aromatic hydrocarbon residue of a dihydric phenol,

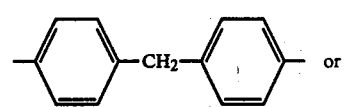 or

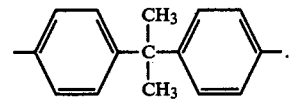

2. The compound claimed in claim 1, wherein X is a residue derived from a dihydric phenol selected from the group consisting of catechol, resorcinol and hydroquinone.

3. The compound claimed in claim 1, wherein X is

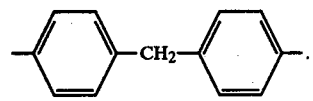

4. The compound claimed in claim 1, wherein X is

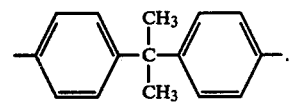

5. A curable epoxy resin composition comprising (a) an epoxy resin having an average of more than one epoxy group per molecule and (b), as curing agent, a compound having the formula

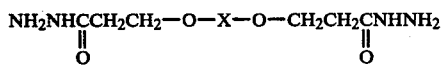

wherein X is an aromatic hydrocarbon residue of a dihydric phenol,

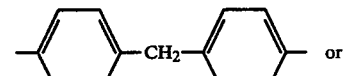 or

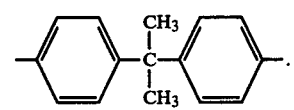

6. The curable epoxy resin composition claimed in claim 5 wherein the amount of said compound is enough to provide 0.5–1.5 times active hydrogen equivalent weight based on epoxy equivalent weight.

7. The curable epoxy resin composition claimed in claim 5, wherein X is

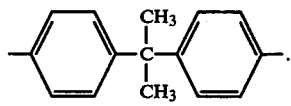

8. The curable epoxy resin composition claimed in claim 5, wherein said epoxy resin is a polyglycidyl ether of a polyhydric phenol.

9. A cured resin obtained by contacting an epoxy resin having an average of more than 1 epoxy group per molecule with as curing agent a compound having the formula

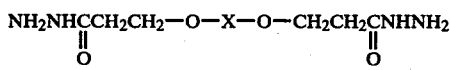

wherein X is an aromatic hydrocarbon residue of a dihydric phenol,

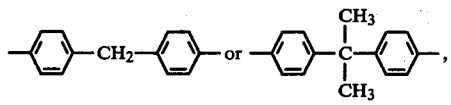

the amount of said compound being enough to provide 0.5–1.5 times active hydrogen equivalent weight based on epoxy equivalent weight.

10. A method of curing an epoxy resin composition, which comprises:

mixing a compound having the formula:

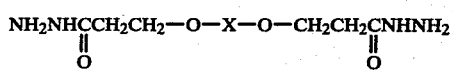

wherein X is an aromatic residue of a dihydric phenol,

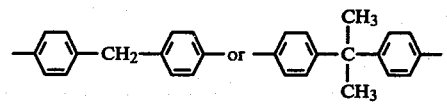

with said epoxy resin composition to give a curable epoxy resin composition, and
heating said curable epoxy resin composition to a temperature of no more than 150° C.

11. The method of claim 10, wherein said heating is to 120°–140° C.

12. The method of claim 10, wherein X is

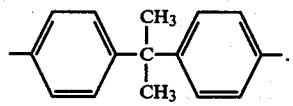

13. The method of claim 11, wherein X is

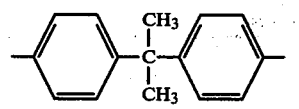

* * * * *